(12) United States Patent
Moriya et al.

(10) Patent No.: US 8,334,878 B2
(45) Date of Patent: Dec. 18, 2012

(54) MEDICAL IMAGE PROCESSING APPARATUS AND MEDICAL IMAGE PROCESSING PROGRAM

(75) Inventors: Yoshiyuki Moriya, Minato-ku (JP); Hideyuki Sakaida, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 883 days.

(21) Appl. No.: 12/377,530

(22) PCT Filed: Jul. 24, 2007

(86) PCT No.: PCT/JP2007/064512
§ 371 (c)(1),
(2), (4) Date: May 19, 2009

(87) PCT Pub. No.: WO2008/020531
PCT Pub. Date: Feb. 21, 2008

(65) Prior Publication Data
US 2010/0231605 A1   Sep. 16, 2010

(30) Foreign Application Priority Data
Aug. 16, 2006   (JP) .................................. 2006-221922

(51) Int. Cl.
*G09G 5/14*   (2006.01)
(52) U.S. Cl. ....................................................... 345/619
(58) Field of Classification Search ................... 345/619
See application file for complete search history.

(56) References Cited

U.S. PATENT DOCUMENTS

| | | | | |
|---|---|---|---|---|
| 5,214,685 | A * | 5/1993 | Howells | 378/34 |
| 6,332,087 | B1 * | 12/2001 | Svenson et al. | 600/407 |
| 6,493,415 | B1 * | 12/2002 | Arai et al. | 378/4 |
| 6,587,541 | B2 * | 7/2003 | Menhardt | 378/62 |
| 7,317,819 | B2 * | 1/2008 | Janes | 382/128 |
| 8,115,171 | B2 * | 2/2012 | Blevis | 250/363.02 |
| 2005/0055184 | A1 * | 3/2005 | Barbour et al. | 703/2 |
| 2006/0018827 | A1 * | 1/2006 | Dadachova et al. | 424/1.11 |
| 2007/0098241 | A1 * | 5/2007 | Wang et al. | 382/128 |

(Continued)

FOREIGN PATENT DOCUMENTS

JP   08-294485 A   11/1996

(Continued)

OTHER PUBLICATIONS

Japanese Office Action corresponding to Japanese Patent Application No. 2006-221922, dated May 17, 2011.

*Primary Examiner* — Javid A Amini
(74) *Attorney, Agent, or Firm* — Sughrue Mion, PLLC

(57) ABSTRACT

A medical image processing apparatus capable of aligning, among plural series of images, slice images included in the series easily in a short time. The medical image processing apparatus is connected to at least one display unit that displays a medical image on a screen based on inputted image data, for correlating anatomically tomographic positions of axial images among plural series of images, and includes: a standard coordinate system and feature quantity storage unit for storing a standard coordinate system in which coordinate values correlated to anatomically tomographic positions of an object to be inspected are set; and a feature quantity computing unit, a coordinate value searching unit, and a slice coordinate determining unit for providing coordinate values in the standard coordinate system to the axial images included in each of the plural series of images.

22 Claims, 12 Drawing Sheets

U.S. PATENT DOCUMENTS

2007/0265813 A1* 11/2007 Unal et al. ........................ 703/2
2009/0124903 A1* 5/2009 Osaka ........................... 600/443
2011/0194787 A1* 8/2011 Chun et al. .................... 382/284

FOREIGN PATENT DOCUMENTS

| | | |
|---|---|---|
| JP | 2002014360 A | 1/2002 |
| JP | 2004230193 A | 8/2004 |
| JP | 2005-124895 A | 5/2005 |
| JP | 2005-296436 A | 10/2005 |

\* cited by examiner

STANDARD COORDINATE SYSTEM

FIG.3

| COORDINATE VALUE Z (STANDARD COORDINATE SYSTEM) \ FEATURE QUANTITY | DEGREE OF CIRCULARITY (XA) | AIR REGION (XB) | BONE REGION (XC) | SOFT TISSUE REGION (XD) |
|---|---|---|---|---|
| 5 | 1 | 0 | $XC_{Z=5}$ | $XD_{Z=5}$ |
| 10 | 0.9 | 10 | $XC_{Z=10}$ | $XD_{Z=10}$ |
| 15 | $XA_{Z=15}$ | 8 | $XC_{Z=15}$ | $XD_{Z=15}$ |
| 20 | $XA_{Z=20}$ | 90 | $XC_{Z=20}$ | $XD_{Z=20}$ |
| 25 | $XA_{Z=25}$ | 85 | $XC_{Z=25}$ | $XD_{Z=25}$ |
| 30 | $XA_{Z=30}$ | 70 | $XC_{Z=30}$ | $XD_{Z=30}$ |
| 35 | $XA_{Z=35}$ | 50 | $XC_{Z=35}$ | $XD_{Z=35}$ |
| 40 | $XA_{Z=40}$ | 40 | $XC_{Z=40}$ | $XD_{Z=40}$ |
| 45 | 0.6 | 40 | $XC_{Z=45}$ | $XD_{Z=45}$ |
| 50 | $XA_{Z=50}$ | 20 | $XC_{Z=50}$ | $XD_{Z=50}$ |

MEDICAL IMAGE PROCESSING APPARATUS AND MEDICAL IMAGE PROCESSING PROGRAM

TECHNICAL FIELD

The present invention relates to a medical image processing apparatus for allowing an image display terminal to display axial images based on image data acquired by a medical imaging modality, and relates to a medical image processing program to be used in the apparatus.

BACKGROUND ART

Recent years, many medical images showing the interiors of living bodies have been used in medical diagnoses, and, in order to acquire such medical images, various technologies and apparatuses (modalities) such as an X-ray imaging apparatus, X-ray CT (computed tomography) apparatus, ultrasonic (US) diagnosing apparatus, MRI (magnetic resonance imaging) apparatus, and PET (positron emission tomography) apparatus are widely used. Many of the apparatuses are digitalized, and diagnostic information processing systems within hospitals and so on are being constructed. Further, among the imaging technologies, CT and MRI have achieved significant results in detection and evaluation of lesion parts in living bodies because they can acquire and display axial images of a living body at relatively short intervals. Here, an axial image refers to a tomographic image that shows a surface perpendicular or substantially perpendicular to the body axis of an object to be inspected (so-called cross sectional surface). Hereinafter, the axial image is also simply referred to as "slice image".

When a medical diagnosis is made based on the medical images, in order to observe the change of an affected part over time, slice images obtained by imaging the same part of the same patient at different times may be compared and interpreted. In this case, an image interpretation doctor should search for, with respect to one slice image of interest among one series of images, another slice image showing anatomically the same tomographic image as the one slice image from among another series of images. However, one series of images generated by one imaging include several hundreds or more images, and therefore, the operation requires great effort for the image interpretation doctor.

As a related technology, Japanese Patent Application Publication JP-A-8-294485 discloses an image display system for displaying on an output device plural sets of three-dimensional images including plural tomographic images acquired in plural times of inspection using at least one medical image imaging modality. The image display system includes designating means for designating at least one first pair of tomographic images at substantially identical anatomical tomographic positions from the plural sets of three-dimensional images, tomographic image pair setting means for setting at least one pair of tomographic images at substantially identical anatomical tomographic positions from the plural sets of three-dimensional images based on a tomographic interval of at least one three-dimensional image of the plural sets of three-dimensional images and position information between the first pair of tomographic images, and display control means for allowing the output device to display the set at least one pair of tomographic images.

Further, Japanese Patent Application Publication JP-P2005-124895A discloses an image diagnosing support apparatus for loading plural tomographic images of a chest image of the day (current image) and a chest image in the past (past image) of the same examinee obtained with a medical image imaging apparatus and displaying both images on image display means at the same time. The image diagnosing support apparatus includes extracting means for extracting tracheas and bronchial tubes from the current image and the past image, bronchial bifurcation determining means for respectively determining bronchial bifurcations first bifurcating from the tracheas extracted by the extracting means, and image aligning means for allowing the image display means to display the current image and the past image at the same position in the body axis direction with reference to the current images and the past images corresponding to the bronchial bifurcations respectively determined by the bronchial bifurcation determining means.

As described above, the technique of aligning plural sets of slice images representing anatomically the same sections between two series of images has been known. However, if the alignment is desired for three or more series of images, transformation processing of coordinate systems (alignment processing) between two series of images should be performed with respect to all combinations. For example, in the case where five series of images A-E are aligned with one another, the total twenty times of arithmetic processing between A and B, A and C, . . . , D and E are necessary. Thus, the operation is inefficient, taking a lot of time and effort.

DISCLOSURE OF THE INVENTION

Accordingly, in view of the above-mentioned points, a purpose of the present invention is to provide a medical image processing apparatus capable of aligning, even for three or more series of images, slice images included in the series easily in a short time, and a medical image processing program to be used in the medical image processing apparatus.

In order to achieve the above-mentioned purpose, a medical image processing apparatus according to one aspect of the present invention is a medical image processing apparatus to be connected to at least one display unit that displays a medical image on a screen based on inputted image data, for correlating anatomically tomographic positions of axial images among plural series of images, and the apparatus includes storing means for storing a standard coordinate system in which coordinate values correlated to anatomically tomographic positions of an object to be inspected are set, and coordinate value providing means for providing coordinate values in the standard coordinate system to the axial images included in each of the plural series of images.

Further, a medical image processing program according to one aspect of the present invention is a medical image processing program, embodied on a computer readable medium, for use in a medical image processing apparatus to be connected to at least one display unit that displays a medical image on a screen based on inputted image data, for correlating anatomically tomographic positions of axial images among plural series of images, and the program actuates a CPU to execute the procedures of (a) loading a standard coordinate system in which coordinate values correlated to anatomically tomographic positions of an object to be inspected are set, and (b) providing coordinate values in the standard coordinate system to the axial images included in each of the plural series of images.

In this application, each axial image is referred to as "slice image" and a group of axial images included in one series is referred to as "series of images".

According to the present invention, since the coordinate values in the standard coordinate system related to anatomically tomographic positions are provided to plural slice images included in each of the plural series of images, alignment between plural series of images can be easily performed via the standard coordinate system. Further, the direct processing such as coordinate transform between series of images is not necessary, and, even alignment among three or more series of images can be efficiently processed with less effort.

BRIEF DESCRIPTION OF THE DRAWINGS

FIG. 3 is a table showing standard feature quantities;

BEST MODE FOR CARRYING OUT THE INVENTION

Figure 1:
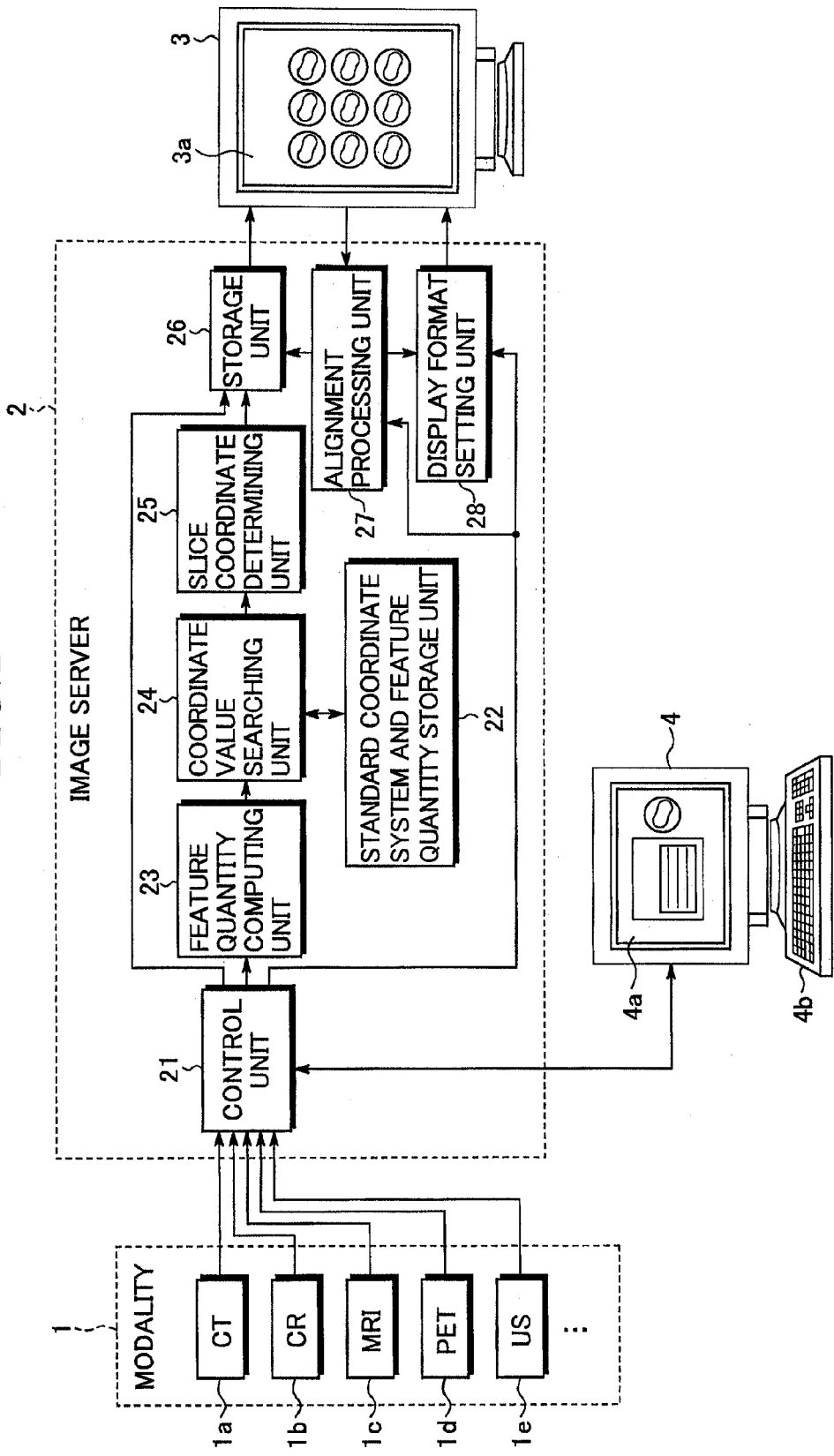
FIG. 1 shows a configuration of a medical image imaging system including a medical image processing apparatus according to the first embodiment of the present invention.

Hereinafter, embodiments of the present invention will be explained in detail by referring to the drawings. The same reference numerals are assigned to the same component elements and the explanation thereof will be omitted.

FIG. 1 is a block diagram showing a configuration of a medical image imaging system including a medical image processing apparatus according to the first embodiment of the present invention. The medical image imaging system includes a modality 1 for performing imaging inspection of medical images on an object to be inspected, an image server 2, an image display terminal 3, and an image interpretation terminal 4. These devices 1-4 are compliant with the DICOM (Digital Imaging and Communications in Medicine) standards.

The modality 1 includes a medical image imaging apparatus such as a CT apparatus $1a$, a CR (computed radiography) apparatus $1b$, an MRI apparatus $1c$, a PET apparatus $1d$, and a US (ultrasonic) diagnosing apparatus $1e$, and so on. These modalities $1a$-$1e$ generate image data by performing imaging inspection and output the image data together with image incidental information to the image server 2. For example, the image incidental information includes patient information (name, age, sex, and so on), imaging date information, part information (head part, chest part, abdomen part, and so on), information representing image orientation ((0020,0037): Image Orientation (Patient)) or (0020,0020): Patient Orientation), information representing the thickness of a slice ((0018,0050): Slice Thickness), and so on. Here, the contents in the parentheses express DICOM tags and attribute names of the respective information.

The image server 2 is a PACS (Picture Archiving and Communication System) server for storing and managing image data acquired by the modality 1. The image server 2 has a function of alignment between plural series of images (alignment processing function) in addition to the normal function of the image server (storing image data and so on), and also operates as a medical image processing apparatus for alignment. The image server 2 outputs image data to the image display terminal 3 according to the request of the image interpretation terminal 4, which will be described later. The function and operation of the image server 2 will be explained in detail later.

The image display terminal 3 is a terminal device for displaying inspection images based on the image data externally inputted and has a high-definition display. Further, the image display terminal 3 may include an input device (e.g., input button, keyboard, mouse, or the like) for a user to input commands. Axial images are schematically shown on a screen $3a$ of the image display terminal 3 shown in FIG. 1.

The image interpretation terminal 4 is a device to be used by the user (image interpretation doctor) for generating image interpretation reports and so on while referring to inspection images displayed on the image display terminal 3, and includes a screen $4a$ for displaying image interpretation reports, an input device $4b$ such as a keyboard, and so on.

Next, the function and alignment processing operation of the image server 2 will be explained. As shown in FIG. 1, the image server 2 has a control unit 21, a standard coordinate system and feature quantity storage unit 22, a feature quantity computing unit 23, a coordinate value searching unit 24, a slice coordinate determining unit 25, a storage unit 26, an alignment processing unit 27, and a display format setting unit 28. Among them, the control unit 21, the feature quantity computing unit 23 to slice coordinate determining unit 25, and the alignment processing unit 27 to display format setting unit 28 are configured by a CPU (central processing unit) and a program, and the alignment processing operation explained as below is executed by the CPU according to a medical image processing program according to the embodiment stored in the storage unit 26.

The control unit 21 allows the storage unit 26 to store the image data and image incidental information thereof outputted from the modality 1. Further, the control unit 21 confirms the orientation of the images (axial, coronal, sagittal, or the like) represented by the inputted image data, and also outputs the image data and the image incidental information to the feature quantity computing unit 23 when the orientation is axial. The orientation of images is acquired from image incidental information provided with DICOM tag (0020,0037): Image Orientation (Patient) or (0020,0020): Patient Orientation.

The standard coordinate system and feature quantity storage unit 22 stores prepared one or some standard coordinate systems and standard feature quantities in the respective coordinate values in the standard coordinate systems. The standard coordinate system is a coordinate system in which coordinate values correlated to anatomically tomographic positions of the object are set, and which is used as reference when alignment between plural series of images is performed. For example, the positions of the respective parts of the object are expressed as coordinate values on the body axis (Z-axis).

The feature quantity computing unit 23 computes feature quantities of a slice image inputted from the control unit 21. The coordinate value searching unit 24 searches for standard feature quantities best match to the feature quantities computed by the feature quantity calculating unit 23 and a coordinate value in a predetermined standard coordinate system corresponding to the standard feature quantities, and tentatively provides the coordinate value corresponding to the standard feature quantities as a coordinate value of the slice image as an object of analysis. The slice coordinate determining unit 25 refers to the slice numbers included in the image incidental information of the respective slice images, confirms whether or not the slice numbers and the coordinate values are consistent with each other, adds the coordinate values in the standard coordinate system to the image incidental information of the respective slice images, and stores the image incidental information in the image data storage unit 26. Here, the feature quantity computing unit 23 to slice coordinate determining unit 25 correspond to coordinate value providing means for providing coordinate values in the standard coordinate system to axial images included in each of the plural series of images.

The storage unit 26 is, for example, a hard disk drive built in the image server 2, and stores image data and image incidental information thereof, a control program (medical image processing program) for actuating the CPU to perform the alignment operation, and so on under the control of the control unit 21. As the recording medium, not only the hard disk, but also an MO, an NT, a RAM, a CD-ROM, a DVD-ROM, or the like may be used. In this case, a drive unit for driving those recording media is built in the image server 2 or externally connected to the image server 2.

The alignment processing unit 27 correlates the slice images included in the different series of images from each other stored in the storage unit 26 such that the anatomical tomographic positions are matched or substantially matched based on the coordinate values provided to each of the images under the control of the control unit 21. Further, the display format setting unit 28 sets a display format when the series of images correlated in the alignment processing unit 27 are displayed on the image display terminal 3.

Figure 2:
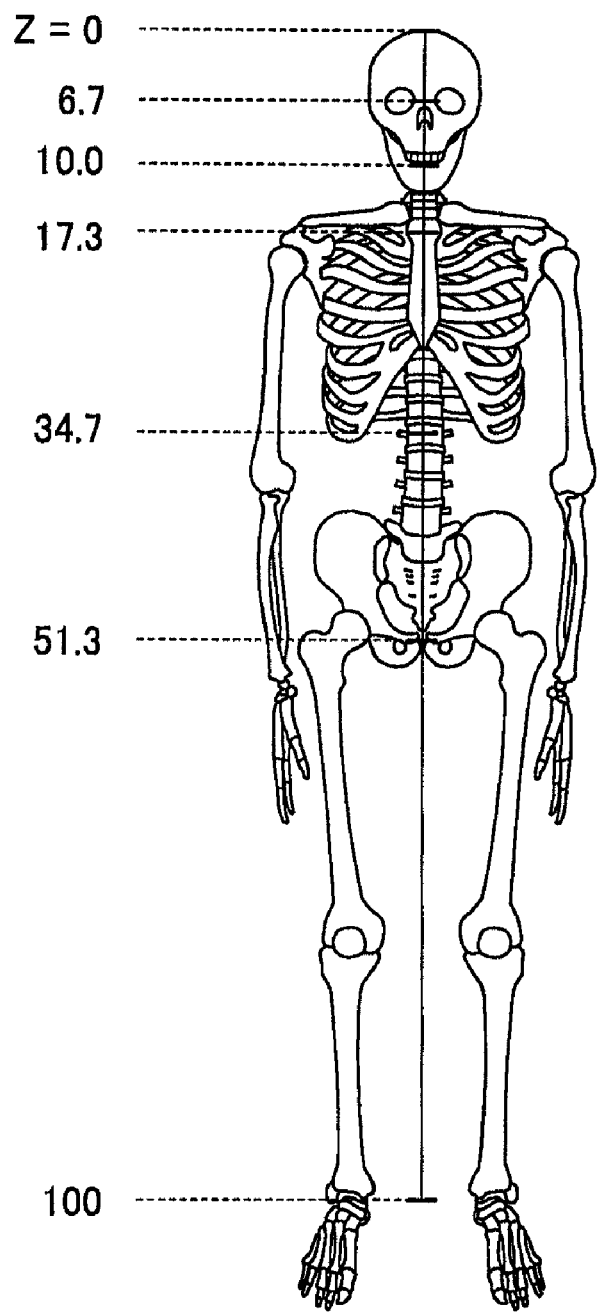
FIG. 2 shows a standard coordinate system for skeleton.

FIG. 2 is a schematic diagram showing a standard coordinate system for skeleton. In the standard coordinate system, the parietal part is represented by Z=0 and the plantar part is represented by Z=100. In this scale, the coordinate value Z of the eyeball is 6.7, the coordinate value Z of the first cervical vertebra is 10.0, the coordinate value Z of the first thoracic vertebra is 17.3, the coordinate value Z of the first lumbar vertebra is 34.7, and the coordinate value Z of the pubic symphysis is 51.3.

As the standard coordinate system, not only the coordinate system referring to the skeleton shown in FIG. 2 but also a coordinate system referring to the location of organs (a standard coordinate system for soft tissue) or the like may be prepared. Further, plural coordinate systems may be prepared according to the respiratory condition (e.g., the expiration condition coordinate system, inspiration condition coordinate system, mean condition coordinate system, and so on). Furthermore, since the balance of the skeleton and the location of organs change according to age, height, sex, and so on, plural coordinate systems may be created according to the classification of the objects (e.g., infant coordinate system, 12-15 year old coordinate system, adult coordinate system, male coordinate system, female coordinate system, and so on).

On the other hand, the feature quantities are obtained by converting anatomical features in one axial section into numerical values from various perspectives. The standard feature quantities of them refer to general (standard) feature quantities in the respective coordinate values of the standard coordinate system. FIG. 3 shows a standard feature quantity table stored in the standard coordinate system and feature quantity storage unit 22. A slice image in a certain coordinate value Z is characterized by standard feature quantities XA, XB, XC, XD explained as below.

Here, regardless of modality, in overall slice images, values computed based on the shapes of the body part (e.g., the degree of circularity) may be used as feature quantities. Further, when the value of each pixel data (i.e., pixel brightness) corresponds to the body property (tissue property or the like), the feature quantity may be computed according to the value. For example, the value of pixel data in a CT image is determined by a CT value, and the CT value is a physical quantity representing the amount of radiation transmitted through the body. The CT value of water is 0 HU, the CT value in the air region is about −1000 HU, and the CT value in the bone region is about 80 HU to 1000 HU, for example. Further, the CT value of a soft tissue such as an organ is higher than that in the air region and lower than that in bone region, about 28 HU to 60 HU, for example.

As shown in FIG. 3, the following four feature quantities are used in the embodiment.

(a) Degree of Circularity of Entire Body Part

The degree of circularity XA is computed by the following equation (1) by using the area S of a target region and the length L around the region.

$$XA = 4\pi S/L^2 \qquad (1)$$

The nearer a perfect circle the shape of the target region becomes, the closer to 1.0 the degree of circularity XA becomes, and the farther from the perfect circle the shape becomes (e.g., the farther from "1" the ellipticity becomes), the smaller the degree becomes. For example, when the target region is the head part, the degree of circularity is relatively high. Contrary, when the target region is the chest or abdomen part, the degree of circularity is relatively low.

(b) Feature Quantity of Air Region

The feature quantity of air region XB is computed by (Number of pixels of CT values representing air region)/(Number of pixels of entire body part). For example, when the target region is the chest part, the air region is relatively wide because of the existence of lungs (40% to 80%). Further, in the abdomen part, the ratio of the air region is lower than that (10% to 40%). Furthermore, when the target region is the head or leg part, the air region is nearly zero.

(c) Feature Quantity of Bone Region

The feature quantity of bone region XC is computed by (Number of pixels of CT values representing bone region)/(Number of pixels of entire body part). For example, when the target region is the abdomen part, the bone region relative to the entire body part is a relatively small range. Contrary, when the target region is the leg part, the bone region occupies the major part relative to the entire body part.

(d) Feature Quantity of Soft Tissue

The feature quantity of soft tissue XD is computed by (Number of pixels of CT values representing soft tissue)/(Number of pixels of entire body part).

Note that, when the above (b)-(d) are employed, it is desirable that the fat regions are excluded from the entire body part. The fat regions vary widely between individuals.

Alternatively, the histogram of pixel values itself or probability distribution corresponding to the modality may be used as standard feature quantities.

The standard coordinate system and the standard feature quantities stored in the feature quantity storage unit 22 are prepared in the following manner, for example.
(i) The standard feature quantities are acquired from anatomically known data disclosed in research papers and so on.
(ii) The standard feature quantities are acquired by analyzing series of images representing a specific object.
(iii) The feature quantities are obtained by extracting series of images, in which anatomical positions of the body parts (the first cervical vertebra, lung apex, and so on) represented in the respective slice images have been specified, from among series of images imaged in the past and analyzing slice images, and mean values of the quantities are used as standard feature quantities.

Figure 4:
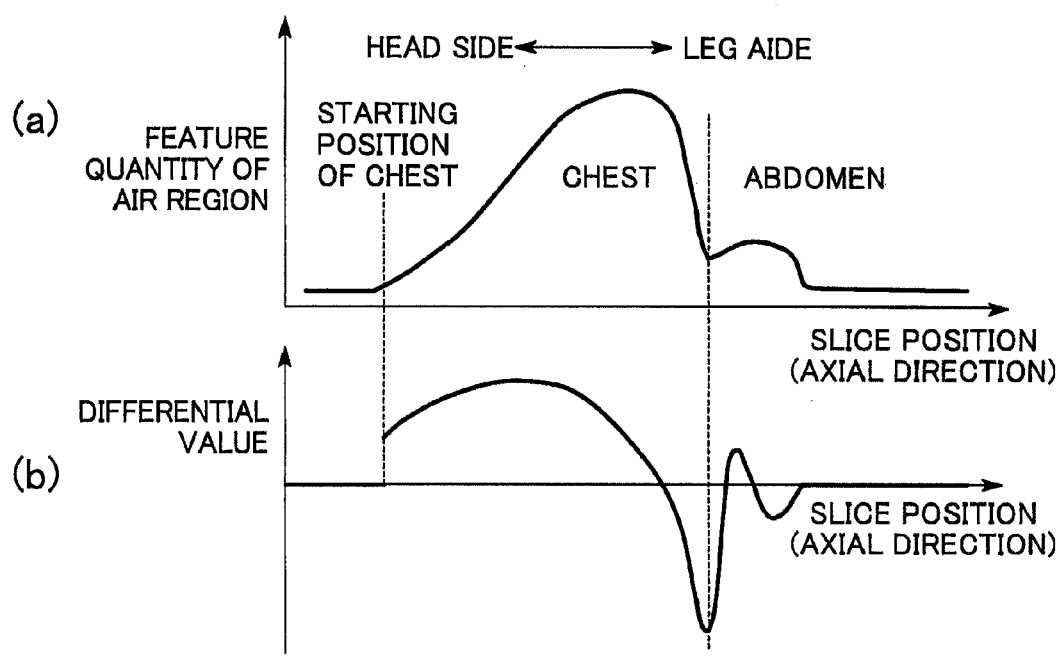
FIG. 4 is a graph showing changes in feature quantities of air region in the body axis direction.

Here, in the case of using the above method (iii), the anatomical positions of the body parts shown may be specified by visual observation of all slice images. Further, as a simpler method, the anatomical positions of several slice images are specified by visual observation at suitable intervals, and the positions of the slice images between those slice images may be determined by the computation using slice interval information in the image incidental information. Furthermore, as another method, the slice image showing the part in the known anatomical position may be manually or automatically recognized. For example, as shown in FIG. 4 (*a*), from the observation of changes in air region as one feature quantity, the position where the air region starts to increase (the start position of the chest part) and the position where the air region abruptly decreases (the boundary between the chest part and the abdomen part) are found. Accordingly, as shown in FIG. 4 (*b*), the characteristic positions (the boundary and so on) may be specified by searching the differential values of the air region computed with respect to one series of slice images. Further, the positions of the slice images between those positions may be determined by the computation using the slice interval information.

The standard feature quantities are prepared with respect to each standard coordinate system when there are plural standard coordinate systems. Further, the standard feature quantities may be prepared with respect to each modality for one standard coordinate system.

Referring to FIG. 1 again, the feature amount computing unit 23 computes the feature quantities of the slice image inputted from the control unit 21. In the embodiment, the feature quantity Xa (the degree of circularity) corresponding to the standard feature quantity XA, the feature quantity Xb (air region) corresponding to the standard feature quantity XB, the feature quantity Xc (bone region) corresponding to the standard feature quantity XC, and the feature quantity Xd (bone region) corresponding to the standard feature quantity XD (soft tissue region) are computed.

The coordinate value searching unit 24 searches for standard feature quantity best match to the feature quantity computed by the feature quantity calculating unit 23 and a coordinate value in a predetermined standard coordinate system corresponding to the standard feature quantity. Then, the coordinate value searching unit 24 tentatively provides the coordinate value corresponding to the standard feature quantity as a coordinate value of the slice image as an object of analysis. The standard coordinate system to be used by the coordinate value searching unit 24 may be designated by the user or selected by the feature amount computing unit 23 according to the image incidental information (patient information, imaged part, or the like).

As methods of searching for a coordinate value, there are the following methods (1) and (2), for example.
(1) Method Using Evaluation Function A predetermined evaluation function is prepared, the standard feature quantity when a value of the evaluation function becomes the minimum is obtained, and the coordinate value in the standard coordinate system corresponding to the standard feature quantity is used as the coordinate value of the slice image. As the evaluation functions, for example, the sum of the absolute values of subtractions between the computed feature quantities and the standard feature quantities $|Xa-XA|+|Xb-XB|+|Xc-XC|+|Xd-XD|$ or the mean square error $\{((Xa-XA)^2+(Xb-XB)^2+(Xc-XC)^2+(Xd-XD)^2)/4\}^{1/2}$ is used. Further, when the value of the evaluation function is computed, weighting may be performed according to the kind of feature quantity.
(2) Method Using Probability Distribution When the probability distribution is prepared as the standard feature quantities, matching of the standard feature quantities is performed by using the probability distribution.

Figure 5:
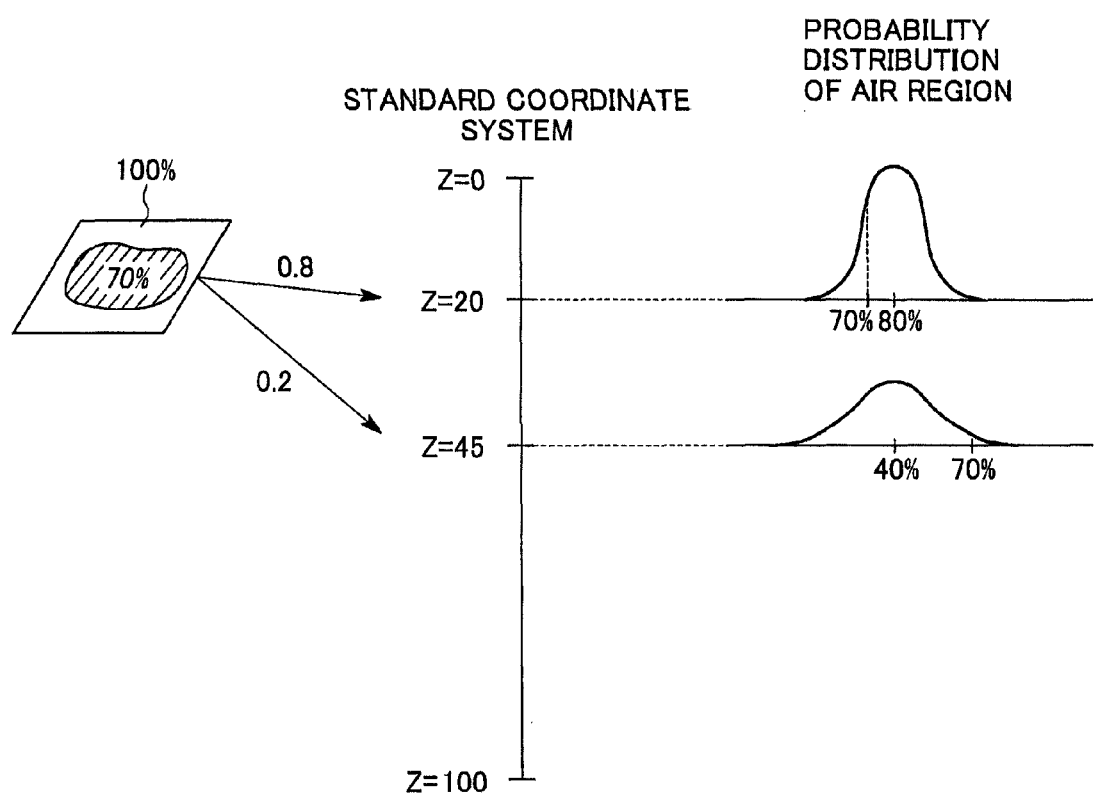
FIG. 5 is a diagram for explanation of a method of obtaining feature quantities based on probability distributions.

Here, referring to FIG. 5, the probability distribution of standard feature quantities of air region at the coordinate Z=20 in the standard coordinate system (mean 80%) and the probability distribution of standard feature quantities of air region at the coordinate Z=45 in the standard coordinate system (mean 40%) are obtained. Assuming that the air region of the slice image as an object of analysis is 70%, it is compared to the probability distributions of the air region at the respective coordinates in the standard coordinate system, the probability that the coordinate of the slice image is Z=20 is 0.8 and the probability that the coordinate of the slice image is Z=45 is 0.2. The analysis using the probability distributions is performed on the other feature quantities, and the probabilities at the respective coordinates are summed and the coordinate with the highest probability is used as the coordinate value of the slice as the target of analysis.

Referring FIG. 1 again, when the coordinate value searching unit 24 tentatively provides the coordinate values in the standard coordinate system with respect to one series of slice images, the slice coordinate determining unit 25 refers to the slice numbers included in the image incidental information of respective slice images, and confirms whether or not the slice numbers and the coordinate values are consistent with each other. Then, if the numbers and the values are inconsistent, the slice coordinate determining unit 25 returns those slice images and the tentatively provided coordinate values to the coordinate value searching unit 24, and allows the coordinate value searching unit 24 to search for the coordinate values to obtain the correct order of slice numbers. On the other hand, if the numbers and the values are consistent, the slice coordinate determining unit 25 adds the coordinate values in the standard coordinate system to the image incidental information of respective slice images, and stores the information in the image data storage unit 26.

Figure 6:
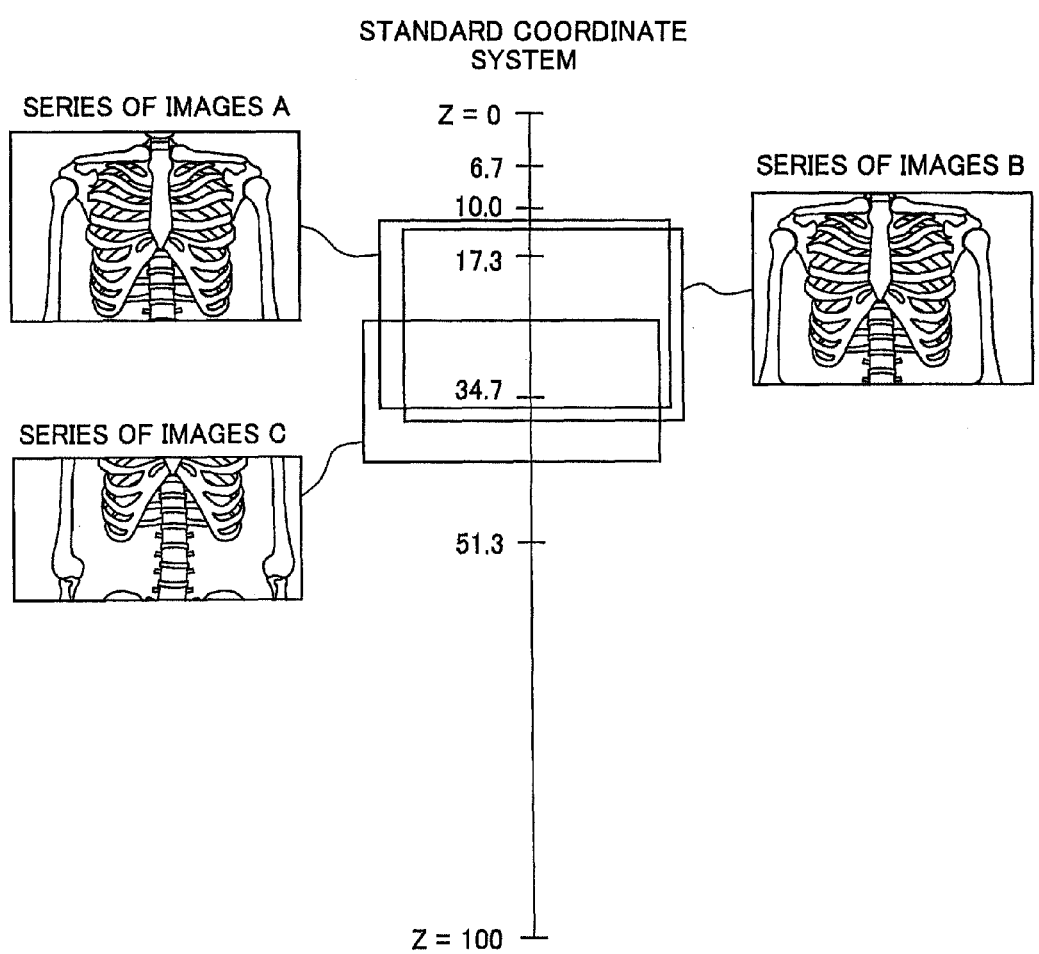
FIG. 6 shows a concept of correlation of a series of images to a standard coordinate system.

By performing the above-mentioned operation on the respective series of images outputted from the modality 1, the series of images A-C that have been separately imaged are correlated to the standard coordinate system as shown in FIG. 6.

The alignment processing unit 27 correlates the slice images included in the different series of images from each other stored in the storage unit 26 such that the anatomical tomographic positions are matched or substantially matched based on the coordinate values provided to each of the images under the control of the control unit 21.

Further, the display format setting unit 28 sets a display format when the series of images correlated in the alignment processing unit 27 are displayed on the image display terminal 3.

The methods of alignment processing performed by the alignment processing unit 27 and the display formats set by the display format setting unit 28 are the following (1)-(7).

(1) Method of Display of Corresponding Slice Images by Manual Input

Figure 7:
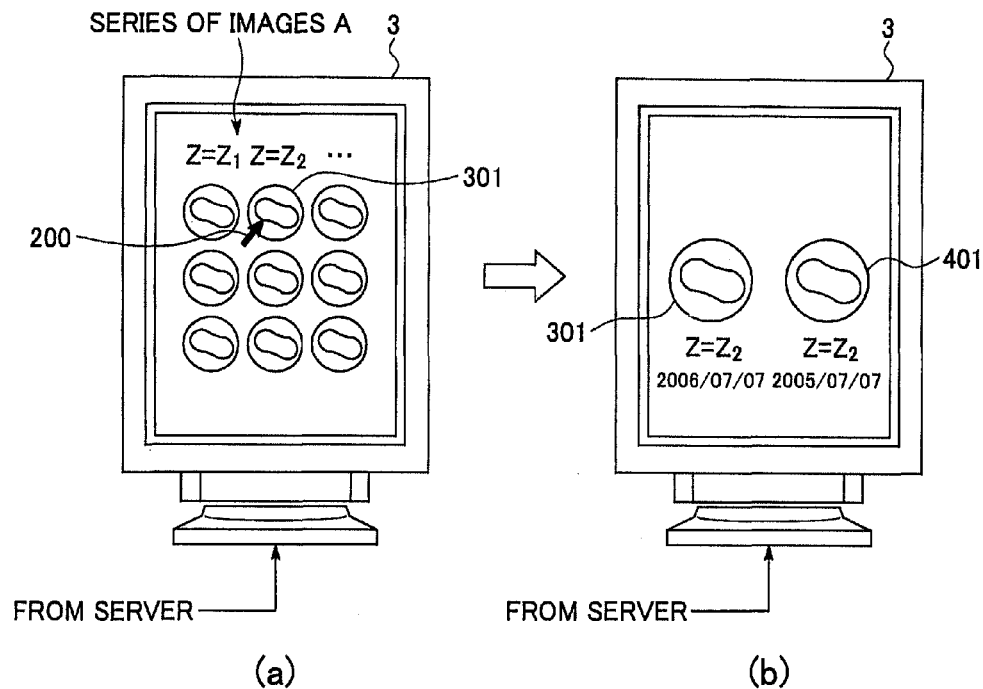
FIG. 7 is a diagram for explanation of a method of displaying corresponding slice images by manual input.
Figure 8:
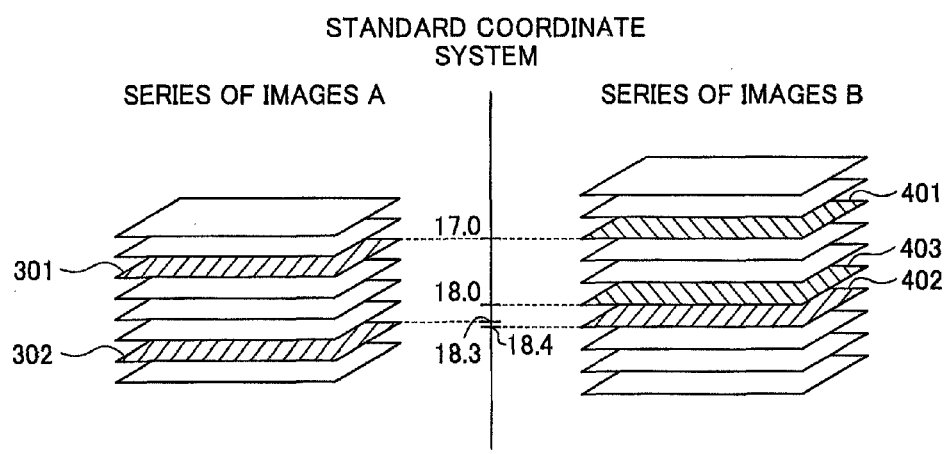
FIG. 8 is a diagram for explanation of alignment of slice images via the standard coordinate system.

For example, as shown in FIG. 7 (*a*), when the user in image interpretation of the series of images A desires to refer to slice images imaged in the past showing the same section as that of a slice image 301 of the series, the user places a cursor 200 on the slice image 301 and clicks it. Thereby, the command of displaying the slice image corresponding to the slice image 301 is inputted to the image server 2. In response, as shown in FIG. 8, the alignment processing unit 27 acquires a coordinate value (e.g., $Z=Z_2=17.0$) in the standard coordinate system from the image incidental information of the slice image 301 and searches for the slice image provided with the coordinate value $Z=17.0$ from the series of images B imaged with respect to the same patient in the past. Then, if there is the slice image provided with the coordinate value $Z=17.0$, the unit allows the storage unit 26 to output the slice image 401 to the image display terminal 3. Thereby, as shown in FIG. 7 (*b*), the slice image 401 that is in the equal anatomically tomographic position to that of the slice image 301 is displayed on the screen of the image display terminal 3.

As the display format of two slice images, the slice image 301 and the slice image 401 may be displayed side by side within one screen as shown in FIG. 7 (*b*), or using two image display terminals 3, the slice image 301 and the slice image 401 may be displayed in the image display terminals 3, respectively. Further, in FIG. 7 (*a*), when the user clicks the plural slice images, the set of correlated plural slice images may be displayed in arrangement. Furthermore, when there are three or more series of images provided with coordinate values in the common standard coordinate system, all of the corresponding slice images among them or a desired number of them according to the designation by the user may be displayed.

Here, in the series of images A and the series of image B, when the slice intervals are different or the values of the coordinate value Z in the standard coordinate system are not equal, the slice image having a desired coordinate value Z may not be acquired. For example, as shown in FIG. 8, regarding a slice image 302 within the series of images A (coordinate value $Z=18.3$), there is no slice image in the strictly the same anatomically tomographic position in the series of images B. In this case, the alignment processing unit 27 searches for a slice image 402 having a coordinate value Z (coordinate value $Z=18.4$) nearest the coordinate value of the slice image 302 and display it. Alternatively, the unit may display two slice images 403 and 402 (coordinate values $Z=18.0$ and $18.4$) located adjacent to the coordinate value $Z=18.3$ of the slice image 302. Furthermore, the slice image at the coordinate value $Z=18.3$ may be newly generated by interpolation processing based on the two slice images 403 and 402. Thereby, slice images in the anatomically tomographic positions substantially equal to that of the slice image 302 can be displayed on the screen of the image display terminal 3.

(2) Method of Display of Subsequent Slice Images by Manual Input

Figure 9:
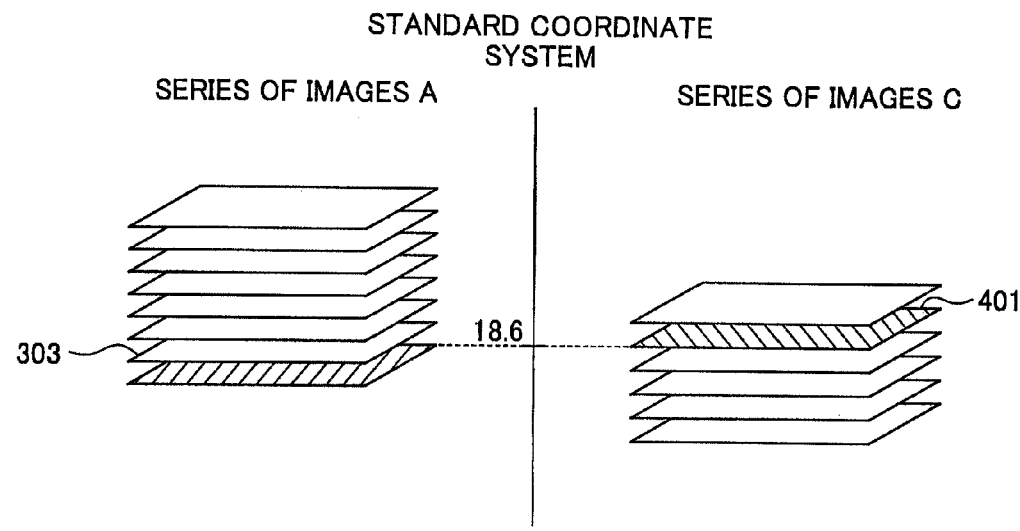
FIG. 9 is a diagram for explanation of a method of displaying subsequent slice images by manual input.

As shown in FIG. 9, when the user desires to refer to the subsequent slice images to a slice image 303 while interpreting the series of images A, the user inputs the command of that to the image server 2. As a method of inputting the command, for example, the user may place the cursor on the slice image displayed on the screen of the image display terminal 3, right-click it, and select a desired command from a pop-up displayed thereby. In response, the alignment processing unit 27 acquires a coordinate value $Z=18.6$ in the standard coordinate system from the image incidental information of the slice image 303, and searches for a slice image at or near the coordinate value $Z=18.6$ from the series of images C that have been imaged with respect to the same patient. Then, the slice image 401 at or near the coordinate value $Z=18.6$ and the subsequent images are displayed on the image display terminal 3.

Figure 10:
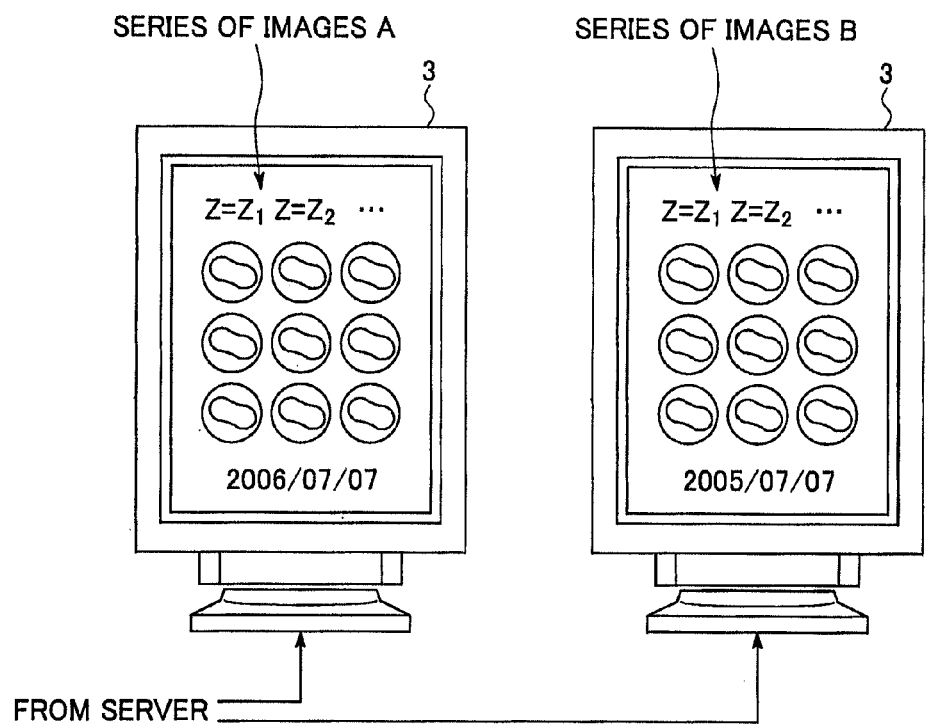
FIG. 10 shows a screen on which the aligned slice images are automatically displayed (stack-displayed) in conjunction with each other.

(3) Method of Automatic Display (Stack Display) of Corresponding Slice Images in Conjunction with Each Other When the user inputs a command of display of the series of images A and B in conjunction with each other to the server 2 (FIG. 1), the alignment processing unit 27 acquires image incidental information of the series of images A and the series of images B from the storage unit 26. Then, the unit correlates the slice images having the equal coordinate value Z based on the coordinate values Z in the standard coordinate system provided to the respective slice images of the series of images A and the coordinate values Z in the standard coordinate system provided to the respective slice images of the series of images B (see FIG. 8). On the other hand, as shown in FIG. 10, the display format setting unit 28 outputs the image data representing the series of images A and B to two image display terminals 3, respectively, and determines the arrangement of the slice images such that the correlated slice images are displayed in corresponding positions on the screen.

As described above, a slice image within one series of images may not be strictly correlated to a slice image within the other series of images. In this case, as described above, the slice images having the nearest coordinate values Z may be correlated or a slice image having the equal coordinate value Z may be newly generated by interpolation processing. Alternatively, regarding the slice image to which no slice image corresponds, the display space of the corresponding slice image may be blank.

Figure 11:
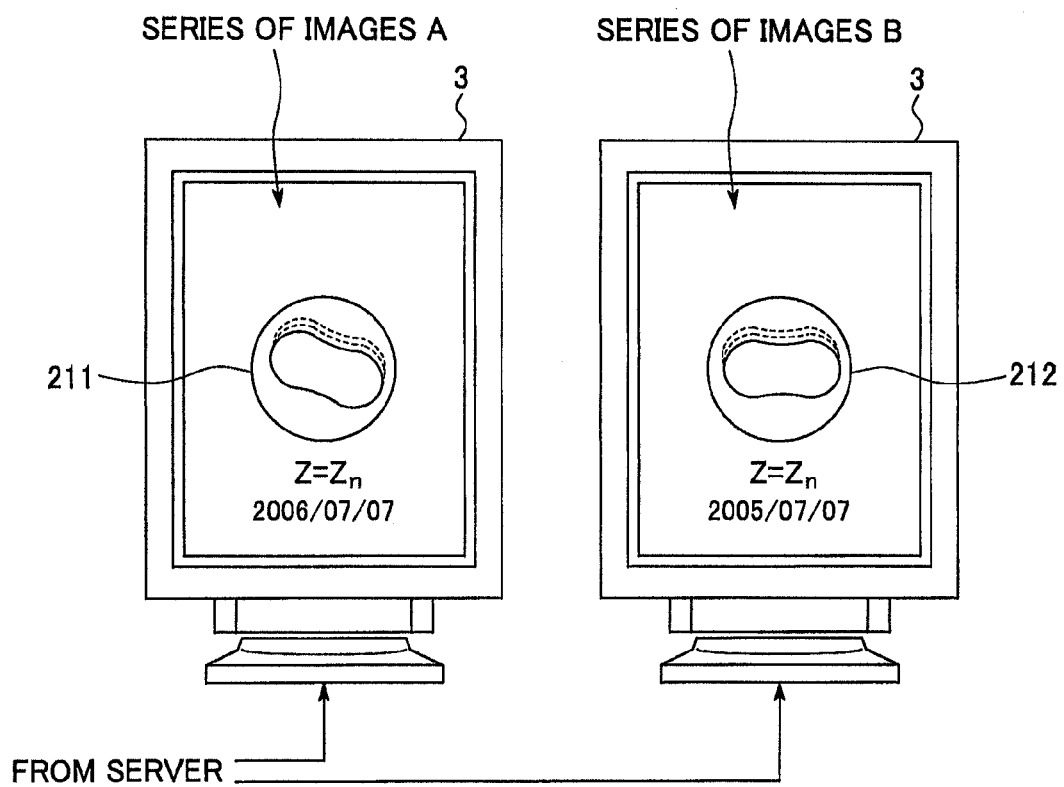
FIG. 11 shows a screen on which the aligned slice images are automatically displayed (cine-displayed) in conjunction with each other.

(4) Method of Automatic Display (Cine Display) of Corresponding Slice Images in Conjunction with Each Other When the user inputs a command of cine display of the series of images A and the series of images B in conjunction with each other to the server 2 (FIG. 1), the alignment processing unit 27 correlates the slice images respectively included in the series of images A and B in the same manner as described in the above method (3). On the other hand, as shown in FIG. 11, the display format setting unit 28 outputs the image data representing the series of images A and B to two image display terminals 3, respectively, and switches the display such that the correlated slice images are sequentially displayed at the same timing on the two screens, respectively. Also, in this method, if slice images included in two series may not strictly correlated to each other, the slice images having the nearest coordinate values Z may be correlated or a slice image having the equal coordinate value Z may be newly generated by interpolation processing. Alternatively, regarding the slice image to which no slice image corresponds, the display space of the corresponding slice image may be blank.

In the above methods (3) and (4), the series of images A and B are displayed on two image display terminals 3, respectively, however, two areas may be provided on the screen of one image display terminal 3 and the series of images A and B may be displayed in the two areas, respectively. Further, when there are three or more series of images provided with coordinate values in the common standard coordinate system, all of the corresponding slice images among them or a desired number of them according to the designation by the user may be displayed.

In the above methods (1)-(4), the series of images different from each other are displayed at the same time. In this case, it is desirable that the same display parameters of gradation, rotation, scaling, and so on are used.

(5) Method of Display of Slice Images in Conjunction with Schematic Diagram

Figure 12:
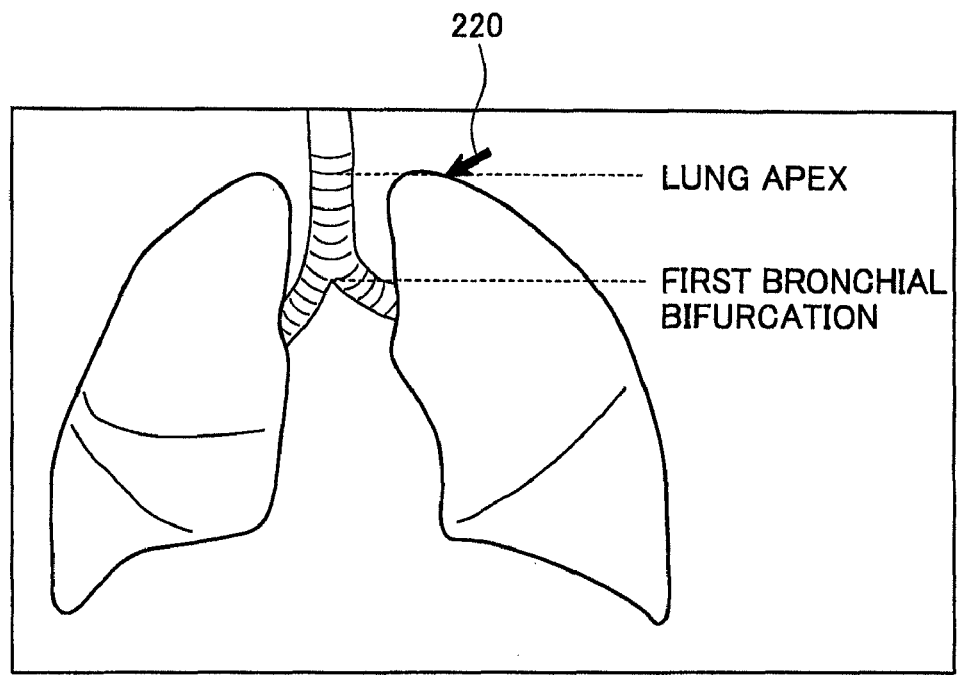
FIG. 12 shows a schematic diagram used in a method of displaying slice images in conjunction with the schematic diagram.

As shown in FIG. 12, a schematic diagram of a human tissue correlated to the standard coordinate system is prepared in advance in the storage unit 26 and the control unit 21 displays the schematic diagram in a part of the screen. Then, when the user places a cursor 220 in a desired position on the schematic diagram and clicks it, the alignment processing unit 27 acquires the coordinate value Z corresponding to the position, searches for a slice image provided with the coordinate value Z from the series of images as an object of image interpretation or the series of images imaged in the past, and outputs image data. Thereby, a slice image showing an anatomical section desired by the user is displayed on the image display terminal 3 (FIG. 1).

(6) Method of Display of Slice Images in Conjunction with List of Parts

Figure 13:
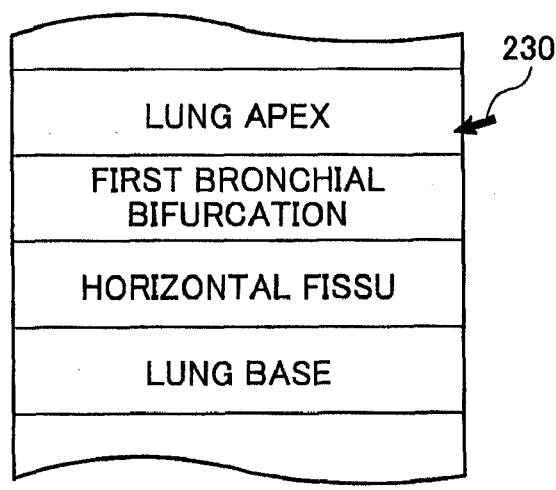
FIG. 13 shows a list of parts used in a method of displaying slice images in conjunction with the list of parts.

In place of the schematic diagram of a human tissue in the above method (5), as shown in FIG. 13, a list of parts correlated to the standard coordinate system may be prepared. For example, when the user places a cursor 230 on the box of "lung apex" and clicks it, the alignment processing unit 27 acquires the coordinate value Z corresponding to "lung apex", searches for a slice image provided with the coordinate value Z from the series of images as an object of image interpretation or the series of images imaged in the past, and outputs image data.

(7) Method of Display of Slice Images in Conjunction with Plain X-Ray Images

In place of the schematic diagram of a human tissue in the above method (5), by correlating plain x-ray images imaged with respect to the same patient of the series of images as an object of image interpretation to the standard coordinate system, the series of images and the plain X-ray images may be conjunction with each other. When coordinate values Z in the standard coordinate system are assigned to the respective parts of the body part shown in the plain X-ray images, known automatic image recognition technology may be used. For example, regarding the chest X-ray images, the lung field recognition technology disclosed in JP-P2005-198887A may be applied.

In the above methods (5)-(7), the slice images are easily conjunction with the schematic diagram or the like desired by the user by using coordinate values in the standard coordinate system, and further, the schematic diagram or the like in conjunction can be easily changed. Furthermore, when the user designates a desired area of the schematic diagram or the like in conjunction, the slice images provided with the coordinate values Z (or the approximate values) corresponding to the area are searched for from the plural series of images, and the images may be displayed at the same time in a format, or, starting from the slice images, corresponding slice images may be stack-displayed or cine-displayed in conjunction with each other.

Figure 14:
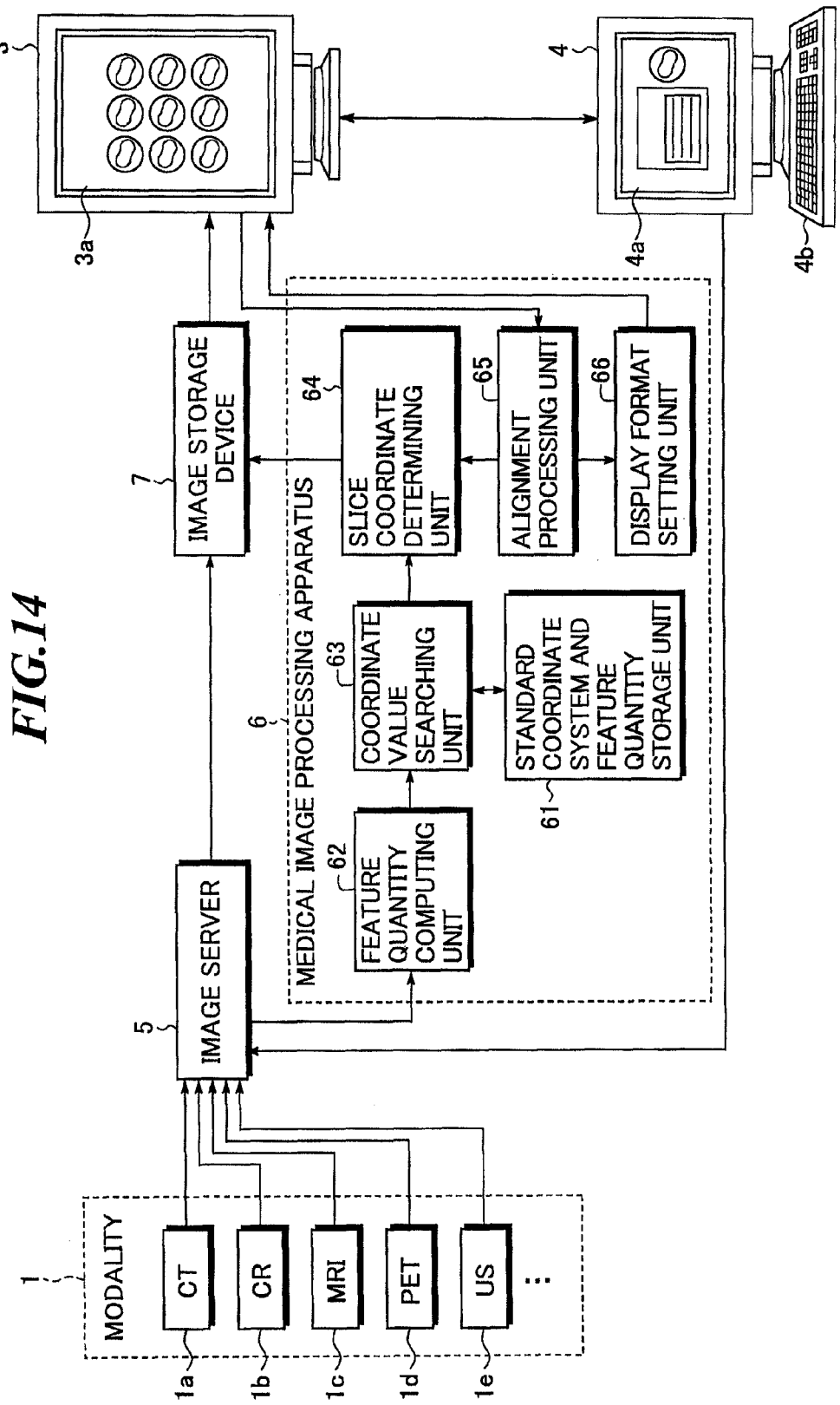
FIG. 14 is a block diagram showing a medical image imaging system including a medical image processing apparatus according to the second embodiment of the present invention.

Next, a medical image processing apparatus according to the second embodiment of the present invention will be explained. FIG. 14 is a block diagram showing a configuration of a medical image imaging system including the medical image processing apparatus according to the embodiment.

As shown in FIG. 14, the system includes an image server 5, a medical image processing apparatus 6, and an image storage device 7 in place of the image server 2 shown in FIG. 1. These parts 5-7 are compliant with the DICOM standards. The rest of the configuration is the same as that in the system shown in FIG. 1.

The image server 5 is a PACS server for storing and managing image data outputted from the modality 1. The image server 5 allows the image storage device 7 to store the image data inputted from the modality 1. Further, the image server 5 outputs the image data to the medical image processing apparatus 6 as well and allows the apparatus 6 to execute alignment processing among plural series of images. Furthermore, the image server 5 controls the image storage device 7 to output the image data stored in the image storage device 7 to the image display terminal 3 according to the request of the image interpretation terminal 4.

The medical image processing apparatus 6 is an apparatus for aligning slice images included in plural series of images among the series, and includes a standard coordinate system and feature quantity storage unit 61, a feature quantity computing unit 62, a coordinate value searching unit 63, a slice coordinate determining unit 64, an alignment processing unit 65, and a display format setting unit 66. The functions and operations of these units are the same as those in the standard coordinate system and feature quantity storage unit 22 to slice coordinate determining unit 25 and the alignment processing unit 27 to display format setting unit 28 as shown in FIG. 1. The medical image processing apparatus 6 is configured by a personal computer (PC), for example.

The image storage device 7 is, for example, a hard disk drive built in the image server 5. Alternatively, as the recording medium, not only the hard disk, but also an MO, an MT, a RAM, a CD-ROM, a DVD-ROM, or the like may be used. In this case, a drive unit for driving those recording media is built in the image server 5. Alternatively, the image storage device 7 is incorporated in the image server 5.

As described above, in the embodiment, the medical image processing apparatus 6 is configured by the PC, and the medical image alignment processing function can be easily incorporated into the existing medical image imaging system. Therefore, desired slice images can be efficiently displayed using the existing equipment.

In the embodiment, the medical image processing apparatus 6 outputs the image data after image processing and their image incidental information to the image storage device 7, however, the image data and the image incidental information may be stored in a storage device (e.g., a hard disk) built in the medical image processing apparatus 6.

Here, in the above explained first and second embodiments, alignment processing is performed on the image data inputted directly from the modality 1 to the image servers 2 and 5. However, the alignment processing may be performed by loading the image data that has been once stored in the recording medium after generated in the modality 1 into the image sever 2 or the medical image processing apparatus 6.

Figure 15:
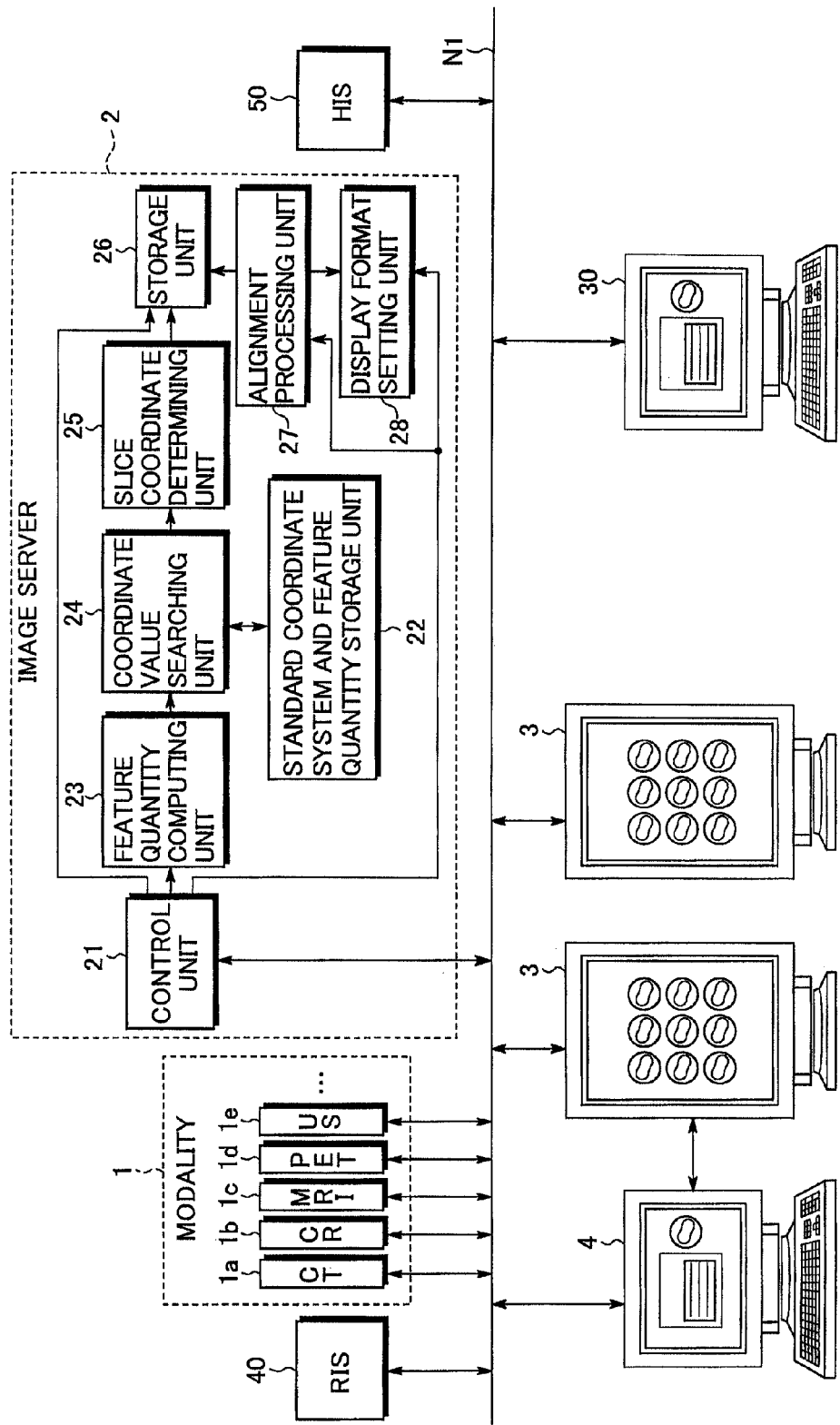
FIG. 15 shows another configuration example of the medical image imaging system including the medical image processing apparatus according to the first and second embodiments of the present invention.

Next, another configuration example of the medical image imaging system including the medical image processing apparatus according to the first and second embodiments of the present invention will be explained with reference to FIG. 15. As shown in FIG. 15, in the system, the modality 1, the image server 2, the image display terminal 3, and the image interpretation terminal 4 are connected to one another via network N1 such as a LAN (local area network). Alternatively, in place of the image server 2, the image server 5, the medical image processing apparatus 6, and the image storage device 7 shown in FIG. 14 may be connected to the network N1. Further, a terminal 30 installed in each department, an RIS (radiology information system) 40, and an HIS (Hospital information System) 50 may be connected to the network N1.

As shown in FIG. 15, by connecting the image server (or the medical image processing apparatus 6) having the medical image alignment processing function to the network N1, the plural series of images aligned to one another can be used in various terminals (e.g., the image interpretation terminal 4 and each department terminal 30), and thereby, efficient image interpretation and medical diagnoses can be performed.

INDUSTRIAL APPLICABILITY

The present invention can be utilized in a medical image processing apparatus for allowing an image display terminal to display axial images based on image data acquired with a medical imaging modality, and a medical image processing program to be used in the medical image processing apparatus.

The invention claimed is:

1. A medical image processing apparatus to be connected to at least one display unit that displays a medical image on a screen based on inputted image data, for correlating anatomically tomographic positions of axial images between plural series of images, said apparatus comprising:
   a storage unit configured to store a standard coordinate system in which coordinate values correlated to anatomically tomographic positions of an object to be inspected are set along a body axis of the object, said standard coordinate system being used as a reference when performing alignment between the plural series of images;
   a coordinate value providing unit configured to provide coordinate values in said standard coordinate system to the axial images included in a first series of images by correlating at least one characteristic position of the object represented in the first series of images to at least one first reference position in said standard coordinate system, and provide coordinate values in said standard coordinate system to the axial images included in a second series of images by correlating at least one characteristic position of the object represented in the second series of images to at least one second reference position in said standard coordinate system; and
   an alignment processing unit configured to correlate the axial images included in the first series of images to the axial images included in the second series of images based on the coordinate values provided to the axial images by said coordinate value providing unit such that anatomically tomographic positions of the axial images are substantially identical between the first series and the second series.

2. The medical image processing apparatus according to claim 1, wherein said standard coordinate system is correlated to at least one of a skeleton and a soft tissue including an organ.

3. A medical image processing apparatus to be connected to at least one display unit that displays a medical image on a screen based on inputted image data, for correlating anatomically tomographic positions of axial images between plural series of images, said apparatus comprising:
   a storage unit configured to store a standard coordinate system in which coordinate values correlated to anatomically tomographic positions of an object to be inspected are set along a body axis of the object, said standard coordinate system being used as a reference when performing alignment between the plural series of images, and standard feature quantities representing anatomical features of body parts in the respective tomographic surfaces correlated to the standard coordinate system;
   a coordinate value providing unit configured to provide coordinate values in said standard coordinate system to the axial images included in each of the plural series of images by computing feature quantities representing anatomical features of body parts shown in the axial images, referring to said standard feature quantities, and thereby, obtaining coordinate values in said standard coordinate system corresponding to said feature quantities, and
   an alignment processing unit configured to correlate the axial images between the plural series of images based on the coordinate values provided to the axial images by said coordinate value providing unit such that anatomically tomographic positions of the axial images are substantially identical between the plural series.

4. The medical image processing apparatus according to claim 3, wherein each of said standard feature quantities and said feature quantities includes at least one of a degree of circularity of the body part, a ratio of air region, a ratio of bone region, and a ratio of soft tissue.

5. The medical image processing apparatus according to claim 3, wherein, when the axial images of a first series provided with the coordinate values by said coordinate value providing unit are displayed on a screen of at least one display unit and a user designates a desired axial image on said screen, said alignment processing unit selects an axial image correlated to the axial image designated by the user among the axial images of a second series different from the first series, and displays the selected axial image on a screen of at least one display unit.

6. The medical image processing apparatus according to claim 3, further comprising:
   a display format setting unit configured to set a display format in said at least one display unit such that axial images correlated between the plural series of images are respectively displayed in corresponding positions on the screen of said at least one display unit.

7. The medical image processing apparatus according to claim 3, further comprising:
   a display format setting unit configured to set a display format in said at least one display unit such that axial images correlated between the plural series of images are sequentially displayed on the screen of said at least one display unit in conjunction with one another.

8. The medical image processing apparatus according to claim 1, further comprising:
   a control unit configured to display a schematic diagram related to said standard coordinate system on a screen of at least one display unit; and
   an alignment processing unit configured to extract, when a user designates a desired area in said schematic diagram, an axial image provided with substantially the same coordinate value as that in said standard coordinate system corresponding to the area, and display the extracted axial image on a screen of at least one display unit.

9. The medical image processing apparatus according to claim 1, further comprising:

a control unit configured to display a list 0 r parts related to said standard coordinate system on a screen of at least one display unit; and an alignment processing unit configured to extract, when a user designates a desired part in said list of parts, an axial image provided with substantially the same coordinate value as that in said standard coordinate system corresponding to the part, and display the extracted axial image on a screen of at least one display unit.

10. The medical image processing apparatus according to claim 1, further comprising:

a control unit configured to display a plain X-ray image related to said standard coordinate system on a screen of at least one display unit; and an alignment processing unit configured to extract, when a user designates a desired area in said plain X-ray image, an axial image provided with substantially the same coordinate value as that in said standard coordinate system corresponding to the area, and display the extracted axial image on a screen of said at least one display unit.

11. A medical image processing program, embodied on a non-transitory computer readable medium, for use in a medical image processing apparatus to be connected to at least one display unit that displays a medical image on a screen based on inputted image data, for correlating anatomically tomographic positions of axial images between plural series of images, said program actuating a CPU to execute the procedures of:

(a) loading a standard coordinate system in which coordinate values correlated to anatomically tomographic positions of an object to be inspected are set along a body axis of the object, said standard coordinate system being used as a reference when performing alignment between the plural series of images;

(b) providing coordinate values in said standard coordinate system to the axial images included in a first series of images by correlating at least one characteristic position of the object represented in the first series of images to at least one first reference position in said standard coordinate system, and providing coordinate values in said standard coordinate system to the axial images included in a second series of images by correlating at least one characteristic position of the object represented in the second series of images to at least one second reference position in said standard coordinate system; and (C) correlating the axial images included in the first series of images to the axial images included in the second series of images based on the coordinate values provided to the axial images at procedure (b) such that anatomically tomographic positions of the axial images are substantially identical between the first series and the second series.

12. The medical image processing program according to claim 11, wherein said standard coordinate system is correlated to at least one of a skeleton and a soft tissue including an organ.

13. A medical image processing program, embodied on a non-transitory computer readable medium, for use in a medical image processing apparatus to be connected to at least one display unit that displays a medical image on a screen based on inputted image data, for correlating anatomically tomographic positions of axial images between plural series of images, said program actuating a CPU to execute the procedures of:

(a) loading a standard coordinate system in which coordinate values correlated to anatomically tomographic positions or an object to be inspected are set along a body axis of the object, said standard coordinate system being used as a reference when performing alignment between the plural series of images, and standard feature quantities representing anatomical features of body parts in the respective tomographic surfaces correlated to the standard coordinate system;

(b) providing coordinate values in said standard coordinate system to the axial images included in each of the plural series of images by computing feature quantities representing anatomical features of body parts shown in the axial images, referring to said standard feature quantities, and thereby, obtaining a coordinate values in said standard coordinate system corresponding to said feature quantities, and (c) correlating the axial images between the plural series of images based on the coordinate values provided to the axial images at procedure (b) such that anatomically tomographic positions of the axial images are substantially identical between the plural series.

14. The medical image processing program according to claim 13, wherein each of said standard feature quantities and said feature quantities includes at least one of a degree of circularity of the body part, a ratio of air region, a ratio of bone region, and a ratio of soft tissue.

15. The medical image processing program according to claim 13, wherein, when the axial images of a first series provided with the coordinate values at procedure (b) are displayed on a screen of at least one display unit and a user designates a desired axial image on said screen, procedure (c) includes selecting an axial image correlated to the axial image designated by the user among the axial images of a second series different from the first series, and displaying the selected axial image on a screen of at least one display unit.

16. The medical image processing program according to claim 13, further allowing the CPU to execute the procedure of:

setting a display format in said at least one display unit such that axial images correlated between the plural series of images are respectively displayed in corresponding positions on the screen of said at least one display unit.

17. The medical image processing program according to claim 13, further allowing the CPU to execute the procedure of:

setting a display format in said at least one display unit such that axial images correlated between the plural series of images are sequentially displayed on the screen of said at least one display unit in conjunction with each other.

18. The medical image processing program according to claim 11, further allowing the CPU to execute the procedures of:

displaying a schematic diagram related to said standard coordinate system on a screen of at least one display unit; and extracting, when a user designates a desired area in said schematic diagram, an axial image provided with substantially the same coordinate value as that in said standard coordinate system corresponding to the area, and displaying the extracted axial image on a screen of at least one display unit.

19. The medical image processing program according to claim 11, further allowing the CPU to execute the procedures of:

displaying a list of parts related to said standard coordinate system on a screen of at least one display unit; and extracting, when a user designates a desired part in said list of parts, an axial image provided with substantially the same coordinate value as that in said standard coordinate system corresponding to the part, and displaying the extracted axial image on a screen of at least one display unit.

20. The medical image processing program according to claim 11, further allowing the CPU to execute the procedures of:

displaying a plain X-ray image related to said standard coordinate system on the a screen of at least one display unit; and extracting, when a user designates a desired area in said plain X-ray image, an axial image provided with substantially the same coordinate value as that in said standard coordinate system corresponding to the area, and displaying the extracted axial image on a screen of at least one display unit.

21. The medical image processing apparatus according to claim 1, wherein said coordinate value providing unit provides coordinate values in said standard coordinate system to the axial images included in a first series of images by correlating plural characteristic positions of the object represented in the first series of images to plural first reference positions in said standard coordinate system, and provides coordinate values in said standard coordinate system to the axial images included in a second series of images by correlating plural characteristic positions of the object represented in the second series of images to plural second reference positions in said standard coordinate system.

22. The medical image processing program according to claim 11, wherein procedure (b) includes providing coordinate values in said standard coordinate system to the axial images included in a first series of images by correlating plural characteristic positions of the object represented in the first series of images to plural first reference positions in said standard coordinate system, and providing coordinate values in said standard coordinate system to the axial images included in a second series of images by correlating plural characteristic positions of the object represented in the second series of images to plural second reference positions in said standard coordinate system.

* * * * *